United States Patent
Burton et al.

(10) Patent No.: US 8,069,852 B2
(45) Date of Patent: Dec. 6, 2011

(54) METHOD AND APPARATUS FOR MAINTAINING AND MONITORING SLEEP QUALITY DURING THERAPEUTIC TREATMENTS

(75) Inventors: David Burton, Camberwell (AU); Eugene Zilberg, Sandringham (AU)

(73) Assignee: Compumedics Limited, Abbotsford, Victoria (AU)

( * ) Notice: Subject to any disclaimer, the term of this patent is extended or adjusted under 35 U.S.C. 154(b) by 1264 days.

(21) Appl. No.: 11/101,878

(22) Filed: Apr. 8, 2005

(65) Prior Publication Data

US 2005/0217674 A1 Oct. 6, 2005
US 2011/0192400 A9 Aug. 11, 2011

Related U.S. Application Data

(63) Continuation of application No. PCT/US03/32170, filed on Oct. 9, 2003.

(60) Provisional application No. 60/417,445, filed on Oct. 9, 2002.

(30) Foreign Application Priority Data

Oct. 10, 2002 (AU) ................................ 2002951984

(51) Int. Cl.
*A61M 11/00* (2006.01)
(52) U.S. Cl. .................................... 128/204.18; 600/529
(58) Field of Classification Search ............. 128/204.18; 600/529
See application file for complete search history.

(56) References Cited

U.S. PATENT DOCUMENTS

| | | | | |
|---|---|---|---|---|
| 6,397,845 | B1 * | 6/2002 | Burton | 128/204.23 |
| 6,431,171 | B1 | 8/2002 | Burton | |
| 6,488,634 | B1 | 12/2002 | Rapoport et al. | |
| 6,502,572 | B1 | 1/2003 | Berthon-Jones et al. | |
| 6,904,913 | B2 * | 6/2005 | Aylsworth et al. | 128/204.22 |
| 2002/0143261 | A1 * | 10/2002 | Nanba et al. | 600/500 |
| 2002/0169384 | A1 * | 11/2002 | Kowallik et al. | 600/529 |
| 2002/0193697 | A1 * | 12/2002 | Cho et al. | 600/529 |

OTHER PUBLICATIONS

Pitson, et al., Use of pulse transit time as a measure of inspiratory effot in patients with obstrcutive sleep apnea, 1995, Eur Repir J, 8, 1669-1674.*
PCT International Search Report, dated Apr. 29, 2004.

* cited by examiner

*Primary Examiner* — Steven O Douglas
(74) *Attorney, Agent, or Firm* — Procopio, Cory, Hargreaves & Savitch LLP (57) ABSTRACT

The present invention monitors and interprets physiological signals and spontaneous breathing events to detect the onset of arousal. Once the onset of arousal is determined, the present invention determines adjustments that are needed in the operation of a therapeutic device to avoid or minimize arousals. In one embodiment, the present invention includes one or more sensors which detect a patient's physiological parameters, a controller which monitors and determines the onset of arousal based on the physiological variables received from the sensor, and a therapeutic treatment device which is controlled by the controller. The sensor can be a combination of one or more devices which are able to monitor a physiological parameter that is used by the present invention to determine the onset of arousal or the onset of a sleep disorder. The sensors can be integrated into one unit or may operate independent of the others.

45 Claims, 6 Drawing Sheets

METHOD AND APPARATUS FOR MAINTAINING AND MONITORING SLEEP QUALITY DURING THERAPEUTIC TREATMENTS

This application is a Continuation of co-pending PCT International Application No. PCT/US2003/032170 filed Oct. 9, 2003, which designated the United States, and on which priority is claimed under 35 U.S.C. § 120, and which claims priority under 35 U.S.C. § 119(a)-(d) to Australian Application No. 2002951984, filed Oct. 10, 2002, and which claims priority under 35 U.S.C. § 119(e) to U.S. Provisional Application No. 60/417,445, filed Oct. 9, 2002.

FIELD OF THE INVENTION

Generally, the invention relates to the field of therapeutic treatments. More specifically, the invention relates to a method and apparatus for delivering therapeutic treatments to patients without adversely affecting their sleep.

BACKGROUND OF THE INVENTION

Many therapeutic treatments are administered to a patient while they are sleeping or are attempting to fall asleep. While these treatments may achieve their intended result, they also often severely affect the quality of sleep that the patient gets while undergoing these treatments. These treatments often interrupt the patient's normal progression of sleep, causing transient arousals. While these arousals do not result in the awakening of the patient, they often pull patients from deeper stages or higher quality states of sleep. Patients often do not reenter these deeper stages of sleep for a relatively long period of time.

In some instances, a therapeutic treatment may cause numerous arousals. This fragments the patient's sleep and prevents the patient from reaching the deeper stages of sleep. Studies have shown that fragmented sleep results in excessive daytime sleepiness. This, in turn, is a direct contributor to many accidents, to a general feeling of lethargy, deterioration of cognitive performance, and/or daytime sleepiness, in the patient.

One example of therapeutic treatments causing sleep fragmentation is in the treatment of sleep disorders. Continuous Positive Air Pressure (CPAP) treatments are a primary remedy for a number of sleep disorders such as sleep apnea, hypopnea, and snoring. CPAP treatments consist of delivering a constant positive airway stream of air pressure into a patient's airway during sleep in order to keep the patient's airway from collapsing upon itself. State-of-the-art CPAP machines, often called auto-titration PAP (APAP) machines, automatically adjust the pressure of the delivered air in order to accommodate a patient's respiratory pattern. to the rapid changes of pressure in the patient's airway caused by the APAP machines. Another drawback of current state-of-the-art APAP machines is that they are subject to either false positives (such as when UAR and/or natural irregular breathing events are not pre-empted or do not occur, despite false detection of such and associated treatment control change) or false negatives (such as when genuine upper airway resistance (UAR) and/or related events are pre-empted or do occur but are not detected or responded to with treatment control change). This is due in part to the reliance of these machines on the correct interpretation of an inspiratory waveform and the inaccuracies related to the interpretation of the underlying waveform by the APAP machine. This can also be due to current state of the art gas delivery (or other treatment control such as pacemaker devices) devices inability to enable suitable algorithms to detect and adapt their computation detection sufficiently to pre-empt or predict the probability or onset likelihood of shallow breathing, UAR, arousals, and or associated sleep fragmentation or sleep quality deterioration.

The inspiratory waveform varies periodically for reasons not always associated with upper airway resistance. The use of inspiratory waveform as the primary or only means of detection of UAR-related events can cause remedial auto titration measures to be taken when none should be. This is particularly evident where the inspiratory waveform analysis technique does not employ an underlying time-course computational method. The time-course computational method refers to comparing a previous sequence of breaths (prestored from previous treatment session or stored from current session breathing data) or the current breath and comparing the variations or changes as an inferred measure of arousal or sleep fragmentation onset. Excessively rapid or excessively insensitive pressure changes often occur when an auto-CPAP machine tries to correct a normal non-UAR related event, or misses detecting the presence of subtle shallow breathing, hypopnea or UAR, respectively. It is believed that the primary cause of sleep fragmentation is the rapid pressure changes in the patient airway produced by the current APAP machines.

In addition to the above, studies have also suggested that some APAP machines are limited in their ability to accurately detect the onset or incidence of shallow breathing, mild hypopnea, or UAR events. This limitation is also possibly attributed to limitations of the machines in interpreting the wave form. Misdiagnosis of such mild hypopnea events results in increased UAR which in turn results in arousal and subsequent sleep fragmentation.

Current state-of-the-art therapeutic devices do not optimally adapt to minimize arousals during therapy. Each patient's arousal threshold is affected by varying parameters, yet current state of the art devices do not have adaptive control algorithms that can adapt their treatment levels to accommodate a number of these varying parameters. These varying parameters include (but are not limited to) sleep history such as sleep deprivation or sleep propensity, physiological factors, psychological factors including (but not limited to) stress or anxiety, environmental factors including temperature; noise; lighting; vibration, factors such as varying threshold to arousals with changing age, drugs and alcohol effects to arousal thresholds and others.

Consequently, in light of the inherent drawbacks in current therapeutic methods for administering treatments to patients who are sleeping or are attempting to sleep, there exists a need for an apparatus and method of monitoring for patient arousal and for adapting a therapeutic treatment to minimize arousal.

SUMMARY OF THE INVENTION

For the purposes of explanation only, the present invention is described primarily in the context of controlling delivery of gas to a patient. One skilled in the art can readily appreciate that the present invention is readily adaptable for use with other therapeutic treatments. The said therapeutic treatments can include ventilatory support or assist devices, oxygen therapy devices or pacemaker devices. As such, it is not intended that this invention be limited to the control of gas delivery.

The present invention is capable of maintaining the sleep quality of a patient undergoing a therapeutic treatment by sensitizing the therapeutic device to various physiological indicators which predict the onset of arousal and using an adaptive algorithm to modify a patient's therapeutic treatment. The therapeutic control algorithm of the present invention has the capability to be adapted during real-time operation based on any combination of a) empirical clinical data, b) individual patient collected or alternative (to laboratory) collected data (from diagnostic study within sleep laboratory or other alternative site) or c) real-time monitored and analyzed data.

In one embodiment, the present invention has a capability to apply empirical clinical data to establish standard threshold configurations, which in turn determine a therapeutic device's response and performance given the current condition of the patient. In the case of a gas delivery device, parameters such as the rate of pressure change, the absolute amount of pressure change, the minimum delivered pressure values and the maximum delivered pressure values can be used. In order to minimize arousals while maintaining the integrity of the treatment, these rates and absolute pressure changes are adjusted in accordance to various patient states including (for example only) the patient's current sleep state or the patient's relative blood pressure or arrhythmia detection. The present invention can be configured to rely on a fixed set of reference data designed to predict the onset or detect the occurrence of arousal.

In one embodiment, the present invention is capable of operating with or without any previous patient data. In the case where a subject has no previous data or threshold indications, the present invention could commence operation with standardized empirical data threshold settings. During device generated pressure changes, or whenever there is a respiratory disturbance or prediction of onset of a respiratory disturbance, the present invention can adapt its control characteristics to minimize the respiratory and arousal disturbance. Control characteristics refer to the rate and absolute pressure changes delivered to a subject together with the devices sensitivity to detect subtle hypopnea, shallow breathing, or UAR. Respiratory disturbance, arousal or upper airway resistance can be detected with an airflow shape monitor, or more comprehensive combinations of physiological monitored channels. In the simplest configuration the present invention would record and note the likelihood of arousal or upper airway flow limitation by way of the shape characteristics of the airflow signal (as derived from a breathing mask circuit). This detection of waveshape characteristics could be achieved by detecting changes in the sequence (1 or more) breathing waveform shapes and then associating these changes with the onset probability or actual incidence of hypopnea, shallow breathing or UAR.

In one embodiment, the present invention includes an algorithm for detecting variation in airflow shape that could be indicative of the incidence or probable onset of upper airway resistance (UAR) or variations of UAR, respiratory event related arousals (RERA) or treatment event related arousals (TERA). These airflow shape variations (and others) can be detected in the breathing mask of a patient undergoing CPAP, oxygen concentration, ventilation or other gas delivery or ventilation support. The detection capability of airflow shape variations enable the present invention to adopt analysis techniques such as neural networks or other methods that are capable of adopting self-learning and algorithm adaptation techniques.

In one embodiment, self-learning and adaptation techniques are specifically applicable to the detection of RERA and TERA. RERA and TERA can be detected by monitoring cortical or subcortical activity or by detecting airflow wave shapes associated with generation of such RERA's. Alternatively, airflow and shape only analysis methods can be adopted.

In one embodiment, the present invention is adapted to detect UAR, RERA, and TERA in a patient using physiological parameters such as pulse transit time (PTT) pulse arterial tonometry (PAT), plethysmographic wave amplitude, electro-encephalogram (EEG), electro-myogram (EMG) and electro-oculogram (EOG), to name a few.

Utilizing these techniques, a gas delivery pressure device (oxygen concentrator, ventilator, VPAP, CPAP, APAP and others) can predict the UAR, RERA and TERA events or the onset of such events and adjust the treatment to avoid such events.

In one embodiment, the process of detecting and monitoring for arousals could occur simultaneously or in virtual real-time with automated gas delivery treatment algorithms which are able to adapt to reduce or eliminate both sleep breathing disorders and sleep fragmentation. The present invention is able to recognize when the pressure adjustment of the gas delivery device is either too severe and leading to the promotion of RERAs or TERAs or avoid the failure to compensate for less obvious (without comprehensive shape analysis and possibly patient specific calibration) or more subtle SBD such as UARs, hypopnea events, and shallow breathing.

BRIEF DESCRIPTION OF THE DRAWINGS AND FIGURES

For purposes of facilitating and understanding the subject matter sought to be protected, there is illustrated in the accompanying drawings an embodiment thereof. From an inspection of the drawings, when considered in connection with the following description, the subject matter sought to be protected, its construction and operation, and many of its advantages should be readily understood and appreciated.

DETAILED DESCRIPTION OF THE PREFERRED EMBODIMENTS

A. General Overview

The present invention is an apparatus and method for maintaining the sleep quality of a patient undergoing a therapeutic treatment. The present invention monitors and interprets physiological signals and spontaneous breathing events to detect the onset of arousal. Once the onset of arousal is determined, the present invention determines adjustments that are needed in the operation of a therapeutic device to avoid or minimize arousals.

Figure 1:
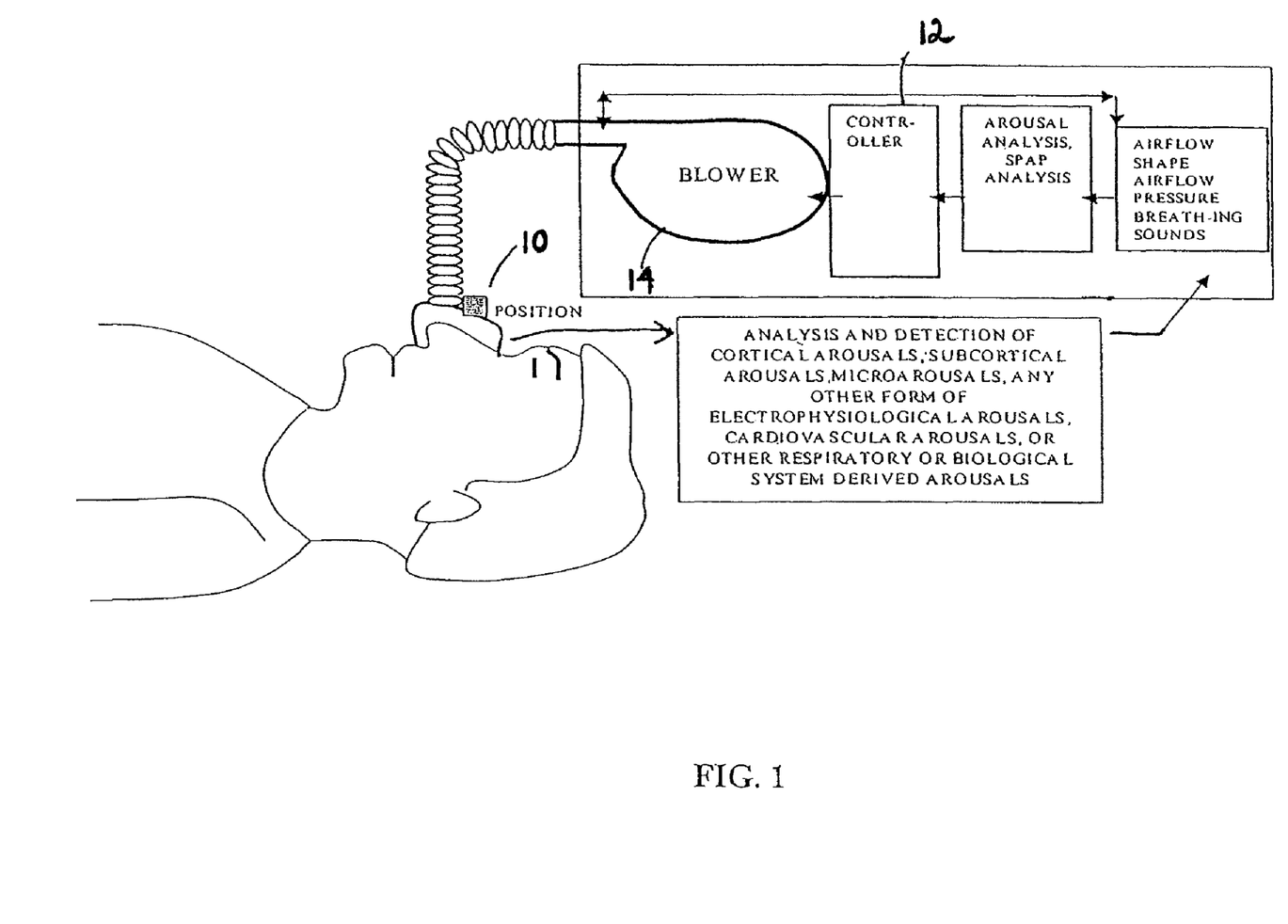
FIG. 1 is a schematic diagram of one embodiment of the present invention.

As shown in FIG. 1, in one embodiment, the present invention includes one or more sensors 10 which detect a patient's physiological parameters, a controller 12 which monitors and determines arousal based on the physiological variables received from the sensor, and a gas delivery apparatus 14 which is controlled by the controller 12. The sensor 10 can be a combination of one or more devices which are able to monitor a physiological parameter that is used by the present invention to determine the onset of arousal or the onset of a sleep disorder. The sensors can be integrated into one unit or may operate independent of the others.

In one embodiment, the present invention is adapted to determine arousal using physiological parameters such as pulse transit time (PTT) pulse arterial tonometry (PAT), plethysmographic wave amplitude, electroencephalogram (EEG), electro-myogram (EMG) and electro-oculogram (EOG), to name a few.

In one embodiment, the present invention is also adapted to monitor, analyze, and compute the sequence of airflow shape and sound. The breathing waveform profiles or sequence of waveform profiles or sounds of a patient are matched to various templates which are correlated to specific arousal events or Sleep Breathing Disorders.

In one embodiment the presence of SBD, UAR, shallow breathing or the onset of the same, can be analyzed and computed.

In one embodiment, the present invention receives a plurality of inputs from sensors and matches the inputs to values listed in a plurality of tables. The tables identify various breathing waveform profiles and physiological parameters or sequence of waveforms and physiological data and matches this information to a particular arousal event or sleep breathing disorder. Furthermore, a number of coefficients and equations can be applied to the values stored in the table in order to accommodate variations which are patient specific.

In one embodiment, the present invention has a capability of operating in three different modes. One mode is a default mode wherein empirical data establishes thresholds and reference data used to compute optimal therapeutic control. The present invention also includes a calibration mode wherein the present invention tests the response of the patient to various settings in order to determine patient tolerances. The present invention also includes an adaptation mode wherein the present invention utilizes optimal therapeutic control in order to minimize or eliminate arousal events or SBD.

B. System Configuration

In one embodiment, the present invention includes three main components, a sensor for monitoring a physiological parameter, a therapeutic device for administering a therapeutic treatment, and a controller for controlling the delivery of the therapeutic treatment. The present invention is described as having three main components for the purposes of explanation only. One skilled in the art can readily appreciate that the three main components of the present invention can be readily integrated into one or more devices.

In one embodiment, the present invention includes a number of sensors, some of which are used to detect upper airway resistance and airflow and some of which detect physiological parameters which are used to determine arousal. The sensor can be any apparatus known in the art which is capable of detecting, measuring, or calculating a physiological parameter which is used to determine arousal. The sensor can be comprised of a single integrated machine or a plurality of independent ones. The sensors can communicate with the controller by any known protocol.

In one embodiment, pressure transducers and a pneumotachograph are used in cooperation or integration with an airtube or a patient mask to detect patient airflow and airway pressure. To detect physiological parameters, the present invention uses sensors such as, but is not limited to, EEG, EOG, EMG, ECG, pulse oximetry, blood pressure, carbon dioxide monitoring, bed transducers for monitoring patient position, video processing systems and microphones for breathing and breathing sounds.

Preferably, the sensors are all incorporated onto a single patient mask. A suitable mask is disclosed in International Publication Number WO 01/43804 entitled "Bio-mask with Integral Sensors," the contents of which are hereby incorporated by reference in its entirety. The mask has sensors integrated therein which are capable of detecting EMG, EEG, EOG, ECG, surface blood pressure, temperature, pulse oximetry, patient sounds, and gas pressure in the mask. The mask can include side-stream or full-stream gas sampling capability for monitoring in real-time, concentration of oxygen, $CO_2$, nitric oxide and other gases or any combination of the aforesaid gases. In addition, the mask serves as the conduit for gas delivery to the patient.

In one embodiment, a mattress device is used to detect arousal. Currently, there are two commercially available mattresses which can perform the above functions. One is known as a Static Charge-sensitive Bed (SCSB) and the other is a polyvinlidene fluoride (PVDF-piezoelectric plastic) bed.

In one embodiment, eye activity is used to monitor arousal. An infrared video monitoring system is employed as a sensor to determine eye activity via eyelid position. The image signal from the video monitoring is processed by graphic processing program to determine the status of the eyes.

In one embodiment, the present invention utilizes a unique multi-standard wireless interface system. Typically, two separate wireless bands are deployed to separate physiological wireless signals from control data. Furthermore, integrated encryption and security may be deployed to avoid unauthorized access to data.

An example of the typical embodiment could be where the 2.4 GHz ISM band is applied for the interface of wireless based sensors interfaced to a controller. Less critical data, not effecting the patient therapy, such as user data viewing and reports, could be interfaced using W-LAN and even Bluetooth™ wireless devices. The multi-radio standard is a particularly important consideration where operating with existent wireless systems. A further capability of the present invention is to detect interference from similar radio band system and switch the critical signal and other monitoring either to an alternate band or modify the system analysis adaptation without wireless signals. The present invention can be used with a range of wireless electrode devices to enable easy expansion and access to additional physiological signals.

In one embodiment, the sensors are battery powered for 1 or 2 days while transmitting signals to the controller. The wireless monitoring capability enables the present invention to monitor RERA, TERA, and SBD-related (sleep breathing disorder) signals during a subject's sleep. Furthermore, the ability to monitor these electrodes during a subject's sleep might give some augmented information (in addition to the respiratory airflow, pressure and sound signals normally derived from the subject's mask) and the ability of the SPAP system to provide optimal therapeutic pressure or gas delivery control to minimize RERA or TERA, while also minimizing obstructive sleep apnea-hypopnea (OSAH) and UARs.

This comparison of sleep efficiency during routine CPAP or enhanced (additional wireless signals applied, for example) CPAP operation can provide valuable information to the healthcare worker and patient in terms of sleep efficiency options for the patient. In a similar manner the patient may choose to utilize a wireless position sensor which could be attached to the therapeutic breathing mask or other parts of the patient therapeutic equipment or clothing.

The said wireless electrode contains several key functions enabling this wireless technology to be used with relative trouble-free ease within the patient's home or the clinical environment alike. The present invention electrodes can be packaged such that the removal of the disposable electrode outer package activates the battery. This automatic wireless electrode activation function enables automatic preservation of the battery life, particularly during storage. Use-by dating of the disposable electrode packaging ensures that both the electrode quality and battery life is used within a suitable period of time, protecting the user from battery age deterioration and electrode deterioration. The wireless interfaced electrodes of the present invention can be provided with self-gelled properties to simplify electrode attachment. The disposable self-adhesive (or reusable) electrode systems can be attached by the patient using simple visual guides.

The sensors input their physiological data to the controller (incorporates pre-processing required for treatment control), which receives the data and determines arousal or onset of arousal. In one embodiment, the controller includes an analog processing circuit which converts analog signals from the sensors into a digital signal. The analog processing circuit utilizes known preamplifying, amplifying, conditioning, and filtering configurations to enable the analog sensor signal to be converted into a digital signal. In some instances, the sensor may directly input a digital signal.

In one embodiment, the controller also includes a processor which receives the digital signal and determines the patient state and an appropriate setting for the gas delivery or other therapeutic device. The processor employs a plurality of tables stored in a database. The tables include a plurality of entries which correlate the inputted signal from a sensor with arousal. Typically, a number of different physiological parameters are inputted simultaneously and all of the parameters are factored in determining arousal. The processor can employ a weighting system for each parameter and the appropriate action is determined by the derived index value. In another embodiment, the processor can link a chain of physiological values together and compare it to a table which correlates the linked set of values to arousal.

In one embodiment, the present invention includes memory devices containing tables holding stored profiles containing normal or acceptable limits for physiological parameters such as:

sleep fragmentation, apnea-hypopnea index (AHI), RERA, sleep architecture, cortical arousals, sub-cortical arousals, PTT values, PAT values, HRV values, central sleep apnea (CSA) occurrence, apnea occurrence, mixed apnea occurrence, hypopnea occurrence, EEG spike occurrence, EEG spindle occurrence, EEG K-complex occurrence, EEG seizure occurrence, bi-coherence or bispectral index values, auditory evoked potential index, patient posture optimal pressure values, patient sleep propensity, patient sleep state.

The controller communicates with the therapeutic device to control the treatment level to the patient. The controller determines an appropriate instruction set by using treatment levels found in the table entry corresponding to the patient's physiological condition. The processor then communicates the instruction set to the gas delivery apparatus which then executes the instruction set.

B. Arousal Monitoring

Figure 2:
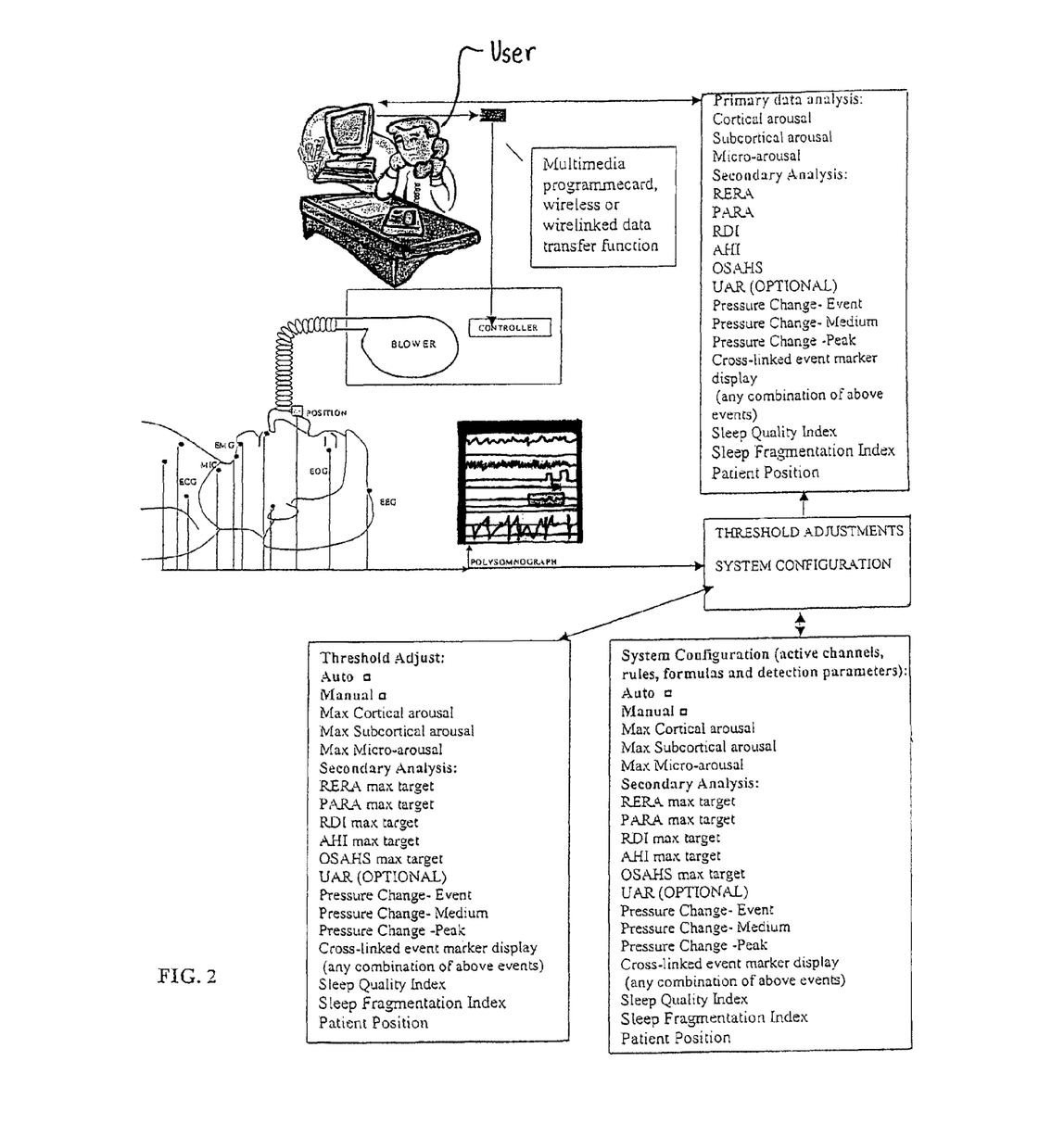
FIG. 2 is a schematic diagram of the arousal monitoring functions of the present invention.

As shown in FIG. 2, the present invention uses various physiological inputs to determine arousal in a patient and to tailor the delivery of air to the patient to minimize such arousal. Due to the complex and varying states of sleep and broad range of sleep disorders that can be diagnosed, many different physiological parameters may be monitored and analyzed to determine arousal.

The minimization of arousals includes the capability to automatically adjust the therapeutic treatment while monitoring at least one physiological parameter or signal where the monitored physiological parameter(s), signal(s) or measures can include (but are not limited to):

Blood pressure, patient movement, patient vibration, patient tremor, patient shake, Pulse oximetry, pulse-wave, EEG, EOG, EMG, patient position, patient movement, breathing sounds, airflow signal, respiratory effort signal(s), pharyngeal pressure signals, expired $PCO_2$ signal, diaphragmatic EMG, transthoracic impedance, electrocardiogram (ECG), reflective oximetry, pulse oximetry, oxygen saturation, nasal pressure, airflow pressure, breathing mask airflow, breathing mask pressure, breathing mask sound, breathing sound, breathing pressure, respiratory inductive plethysmography, plethysmography-wave, oesophageal pressure, nasal cannular sensor signals, nasal and oral cannular sensor signals, oral cannular sensor signals, thermocouple sensor signals, thermistor sensor signals, PVD temperature sensor signals, PVD sound and vibration sensor signals, PVD breathing or airflow signals, Pneumotach calibrated flow, or other routine or research application of polysomnograph (PSG) monitoring sensors electrodes or signals.

In one embodiment, arousals are monitored using an EEG. Typically, the forebrain is monitored to determine cortical arousals and the brainstem is monitored to measure subcortical arousals. The onset of arousal is characterized by bursts of higher frequency EEG signals or a shift to alpha or theta activity from a slower background frequency, and, occasionally, transient increase in skeletal muscle tone. Standard EEG electrode placements and protocols may be used to measure arousals.

In one embodiment, the present invention includes the capability to distinguish a periodic leg movement (PLM) related arousal from a respiratory related arousal. Distinguishing PLM arousals from arousal associated with respiratory events can be important, particularly where optimum treatment control may not respond to a PLM related arousals but may need to respond to a respiratory event related arousal.

The present invention detects and distinguishes PLM and/or PLM arousals by means of comparing sub-cortical arousals inferred from blood pressure variations with cortical arousals (EEG). Cortical arousals are used to distinguish sleep-fragmentation and neurological related arousals versus sub-cortical arousals which generally include both sleep-fragmentation and neurological related arousals and PLM related arousals.

In one embodiment, the onset of arousal is determined using Pulse Transit Time (PTT). Studies have shown that sleep disorders such as apnea, hypopnea or upper airway resistance result in an accompanying arousal, and this arousal is accompanied by changes in heart rate, a transient burst of sympathetic activity, and a surge in blood pressure. Obstructive sleep apnea can be correlated with an obvious and measurable increase in intrathoracic pressure associated with obstructive effort and cardiobalistogram effect. The cardiobalistogram effect is created when the lungs apply pressure to the heart. This compresses the heart and reduces the volume of blood pumped by the heart. These cardiovascular changes are recognizable by way of a transient but significant dip in the patient's baseline PTT value.

PTT is the time taken for the pulse wave to travel between two arterial sites. The blood pressure is directly proportional to the speed that the arterial pressure wave travels. A rise in blood pressure relates to faster pulse wave and thus shorter PTT. Conversely, a drop in blood pressure results in a slowing of the pulse wave and an increase in PTT.

In one embodiment, PTT is obtained using sensors located on the above-mentioned bio-mask. A sensor receives input from the mask and generates a plethysmography waveform. A second sensor receives input from the mask and generates an ECG signal. The waveform and the signal are inputted into the controller and a PTT reading is calculated.

The PTT is derived by utilizing a plethysmography waveform obtained by using pulse oximetry techniques in combination with an ECG signal. In one embodiment, the ECG R or Q wave can be used as the start point for the PTT measurement and the end point of the PTT measurement can be the point representing 25% or 50% of the height of the maximum pulse wave value.

In one embodiment, EMG measurements are used to detect levels of sleep in a patient. EMG monitoring enables the present invention to detect sleep-related changes in a patient's muscle tonicity. Sleep states will typically be accompanied by changes of tonicity in certain muscles. Arousals will typically result in increased muscle tonicity.

In one embodiment, ECG and an EMG signal from the diaphragm are monitored in combination to detect respiratory effort associated with central apnea versus obstructive apnea. The ECG electrodes are configured on the patient in order to distinguish diaphragm related respiratory effort from thoracic respiratory effort. During central apnea, there will be a cessation of breathing without respiratory effort. This is distinctly different from obstructive apneas wherein muscle activity increases as a result of increased breathing effort to overcome the obstructed airway.

In one embodiment, a patient's eye movements are monitored to assist in determining arousal. One technique involves the use of digital video recording and known graphic processing techniques to determine eye lid activity (i.e. whether the eye lids are closed, open, or degree of openness).

In one embodiment, arousals are detected by monitoring the presence of waveform signal disturbance evident on a high bandwidth analysis (DC to 200 Hz or higher bandwidth) of the airflow waveform and pressure waveform obtained within a breathing mask. Apnea events, shallow breathing, upper airway resistance and hypopnea events can also be detected and preempted by analysis of the change in shape of the high bandwidth monitoring of the airflow waveforms and pressure waveforms.

In addition to monitoring arousal, in one embodiment, other physiological parameters may be monitored to determine the patient's physical state. The present invention can utilize sensors in the biomask to determine heart rate, ECG, respiration rate, snoring sounds, airflow, air pressure, and $O_2$ saturation. Conventional methods may also be incorporated into the present invention to monitor blood pressure, and $CO_2$. The patient's sleeping position may also be monitored using pressure transducers or a mattress device.

In one embodiment, wherein a patient is undergoing CPAP treatment, arousal monitoring also includes monitoring pressure and airflow associated with a patient's breathing in order to determine UAR (which may induce RERA). To prevent RERA, it is necessary to detect a number of patterns which are indicative of sleep apnea symptoms, namely inspiratory flow limitation (flattening), snoring and flow amplitude reduction (hypopneas and apneas). As detailed in FIG. 3, the present invention analyzes the airflow to and from the patient in order to determine the existence of UAR.

Figure 3:
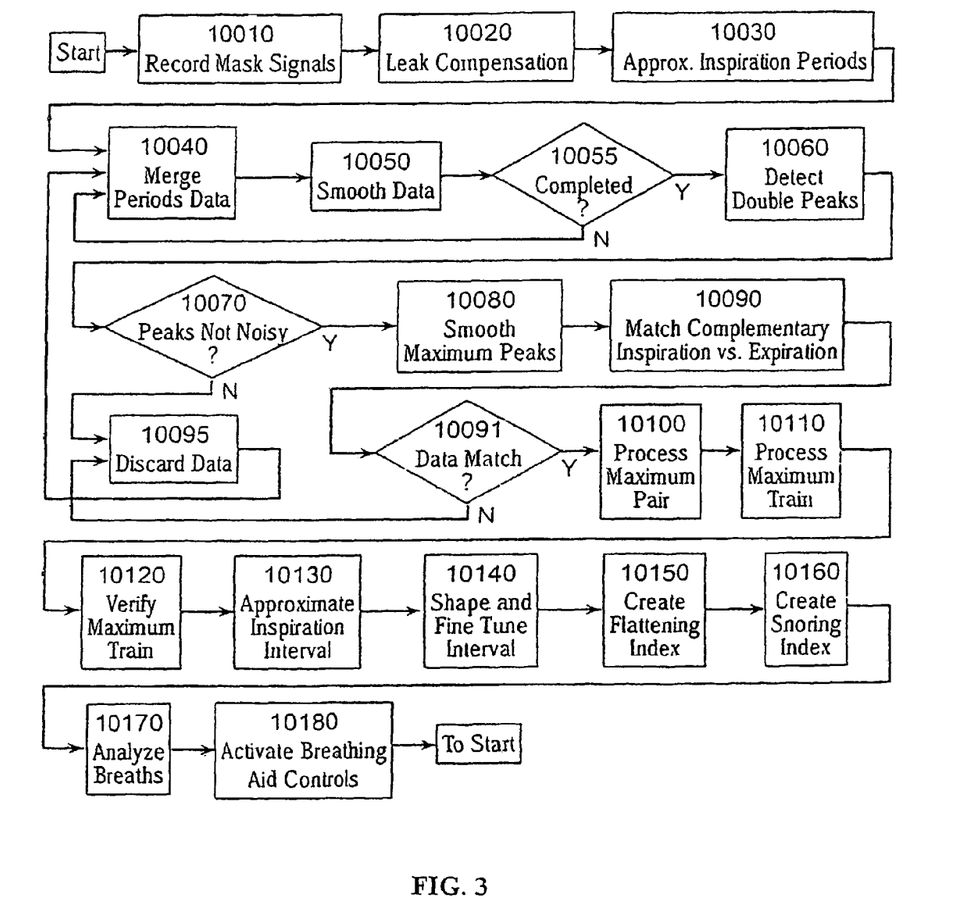
FIG. 3 is a flowchart of the airflow diagnostic process for the present invention.

A "Breath detection" component performs real time detection and characterization of individual breaths. Detection of inspiration and expiration peaks includes "local" smoothing (to separate real breaths from noise) and "global" detection of respiration peaks based on relatively long context which may include up to six consecutive breaths. Breath analysis includes accurate detection of inspiration interval and characterization of flow during inspiration, namely indices of flattening, snoring and inspiratory amplitude as well as a few others.

A "Time interval based processing" component performs analysis of pressure and flow derived signals based on expiration of time intervals rather than breaths. It is necessary in cases when breaths are not discernible such as apneas or when the mask comes off the face.

The controller generates pressure adjustment signal on the basis of per breath and per time interval information provided by the two above components. The controller is implemented as a collection of rules which cover various combinations of indicators of flow limitation, snoring, breath amplitude, pressure leak and other parameters.

In one embodiment, the main strategy in breath detection is to use maximum and minimum points (flow signal level) as the indicators of inspiration and expiration intervals. Inspiration is associated with positive flow signal deflection and expiration is associated with the negative deflection. However, the flow signal could be contaminated by large amount of noise, and it is necessary to smooth flow data before detecting actual breath patterns (box 10050). For accurate detection of the inspiratory and expiratory peaks it is also necessary to use a relatively long context to prevent confusing them with local maxima and minima in the flow signal.

There are two main tasks in the local smoothing. First, all local maximum and minimum points from the flow signal are detected, and each maximum point is defined as an initial candidate for the location of an inspiration peak, and each minimum point for an initial candidate for possible location of expiration peak. The second task is to smooth some maximum and minimum points with "relatively small amplitude", which are likely to be noise signal. As a result of local smoothing, only maximum and minimum points with "relatively large amplitude" are retained, and the flow signal is considered to be sufficiently smoothed. This sequence of local smoothing be described as follows:

1. Detect all local maximum points from a set of flow data.
2. For each maximum point, form a pattern called max-peak, in which the maximum point is located in the center, and data in its left side increase monotonously, and decrease monotonously in its right side. For the current flow data set, obtain a set of max-peak patterns.
3. For the same data set, detect all local minimum points and obtained a serial of min-peak patterns using the similar method.
4. Calculate a number of parameters such as signal variation and duration for each max-peak and min-peak, and these parameters are used as the measurements to test whether some of detected max-peak and min-peak patterns are in fact noise.
5. Analysis sequences of adjacent max-peaks and min-peaks (in every sequence the number of max-peaks should exceed the number of min-peaks by one or alternatively the number of min-peaks should exceed the number of max-peaks by one) and check if a sequence could be approximated by a single max-peak or min-peak so that an approximation error is significantly less than variation and duration parameters of a resulting max-peak or min-peak 6. For the noise signal smoothing, use piecewise linear methods to approximate the flow signal.

7. The max-peaks with relative large amplitudes are retained, and for each "retained" max-peak, both 'increasing period' (left side) and 'decreasing period' (right side) are not shorter than a pre-defined threshold (0.75 s).

8. Same method is applied to min-peak smoothing processing.

The local smoothing is basically designed for excluding noise signals that have a relatively small amplitude and short duration. As a result, a large amount of maximum and minimum points can be excluded from a list of "candidates" for inspiration and expiration peaks. The local smoothing processing can form separate "increasing periods" or "decreasing periods", and the signal within an "increasing period" or a "decreasing period" corresponds to a "likelihood" of the half duration of inspiration or expiration. This "half-duration" smoothing processing is one approach for deleting small noise signal. On the other hand, the "half-duration" approach lacks capability of smoothing flow data containing some relatively large noise and artifacts.

Another difficult problem in breath detection is related to the change of respiration patterns. The flow signal is often affected by patients that change their "way" of breathing, in other words, some periods of the increasing or decreasing signal level are related to change of patient's respiratory "behavior" rather than to inspiration or expiration. Local smoothing is unable to exclude these types of max-peaks or min-peaks. However, it is possible to use some global measurements to effectively detect these "unlikely" max-peaks or min-peaks, and this is the idea behind the global detection of respiratory peaks (global smoothing) (box 10080). In the global smoothing, multiple consecutive breaths are checked to further disqualify some max-peaks or min-peaks from the list of candidates for inspiration or expiration peaks.

For a relatively long time interval (up to 3.5 minutes), conditions are tested for pairs of successive max-peaks (min-peaks as well), and a set of so-called max-pairs (or min-pair) is formed. Then a number of conditions for series of max-pairs to obtain a set of max-pairs with similar 'patterns', denoted as max-train are developed. The same processing is carried out to generate min-trains out of min-pairs. Therefore there are two main parts in the global smoothing, namely generation of max-pairs (min-pairs) (box 10100) and max-trains (min-trains) (box 10110). The following paragraphs outline max-pair and max-train processing briefly (min-pair and min-train generation employ the same respective methods).

From the starting point of the max-peak set, a pair of max-peak patterns is determined, which must meet the following conditions:
 (1). The duration between two max-peaks must be longer than the minimum duration of a breath (0.75 s).
 (2). The duration between two max-peaks must be shorter than the maximum duration of a breath (10 s).
 (3). There is not any intermediate max-peak within a max-pair. An intermediate max-peak pattern is defined as that the signal level of the maximum point in a intermediate max-peak pattern is larger than 80% of signal level of the maximum point in the max-pair itself.
This search processing is carried out through the whole max-peak pattern set to obtain a sequence of max-pairs.
 (4). For each max-pair, a number of statistical measurements are calculated, and these measurements are based on the difference between the original flow signal and the approximation lines within each max-pair.

There are two main outputs in this processing, one is a set of max-pairs which is one step closer to the final set of inspiratory peaks, and another is a number of statistical measurements which is used to represent the "shape" of the max-pair. In the subsequent max-train processing, we will rely on these statistical measurements to carry out 'similarity' test.

The main method used in the max-train processing is called "similarity" test, i.e., we measure the "similarity" within a sequence of max-pairs to form a sequence of max-pairs with "similar" pattern, denoted as max-train. Only the max-pair that passes a "similarity test" can be included into the max-train. The idea behind the max-train is that
 i. A sequence of normal breaths over a successive period of time (3-6 breath durations) should have similar shapes, and this pattern should not be changed significantly over a short period of time as well.
 ii. If a max-pair is not similar to this normal breath pattern, it could be rather like a respiratory event (apnea or hypopnea), or some noise/artifact pattern in flow signal.
The brief algorithm of max-train processing is then as follows:

1. Each candidate max-pair must first meet minimum duration requirement that is defined as the distance between candidate and the reference max-pair.

2. Starting from each single candidate, we calculate a number of parameters such as duration, variation of signal level, the shape of max-peak (or min-peak). We then calculate some statistical measurements for this group of candidates such as mean, deviation, average and maximum error for all the elements to check the similarity among of these candidates.

3. If the condition of the similarity is met, the group of max-pair is formed as a max-train (box 10120). Otherwise, the processing is moved into next max-pair until all max-pair are checked.

4. The same method is applied to the min-train processing.

5. Using max-train and min-train sets, we are now able to detect the locations of global maximum points of flow signal level that are related to the inspiration periods, and a number of minimum point that is associated with the expiration periods.

The global max-peak and min-peak arrays provide estimated locations of each breath, i.e., inspiration and expiration peaks. In order to detect respiratory events, one needs to closely look at these breaths, which includes:

1. Detect the start and end points of inspiration interval (box 10130).

2. Perform flow flattening (box 10150) and snoring analysis (box 10160) as well as calculation of other breath parameters.

During smoothing processing a linear approximation method is used to smooth flow data except of maximum and minimum points in max-train and min-train data sets. However, for purpose of breath analysis 'recover' raw flow data using maximum and minimum points as references is needed prior to carrying out breath analysis processing.

There are two steps involved in detecting inspiration, namely estimation and fine-tune processing. For the inspiratory interval estimation, the assumption is that the amount of in-taking flow during inspiration period should be same as that of 'expiring-out' flow during expiration period. Using the maximum and minimum points in flow signal as references we estimate the interval of inspiration, i.e., the start and end points of inspiration based on calculating the areas of flow data.

However, this method has inherently two problems that could effect the accuracy in inspiration detection. Firstly, when the flow is measured at the mask the amounts of flow during inspiration period and the followed expiration period may not be the same, especially when patients use their mouth to breathe, and we call this problem as "flow imbalance". Secondly, there may be "area insensitivity" problem. When patients start inspiration the flow signal level rapidly increases, but the measurement of flow area is an integration processing that is much slower than the change of flow signals itself. In other words, the change of flow area is not sensitive enough to accurately measure the start point of inspiration where flow signal is changed rapidly.

The flow area is first calculated to estimate the inspiration interval, which includes the start point and the end point of an inspiration. The start point of an expiration period is simply defined as the end point of the previous inspiration period, and the end point of the expiration period is the start point of the following inspiration period or can be ignored as this point does not play any role in our control algorithms. Starting from the estimated start point inspiration period, linear approximation methods to detect the "break point" during flow signal increasing period, and this break point is then defined as the start point of the inspiration interval. The end point of the same inspiration period is simply defined as a point at which the signal level is the same as that of the start point of the inspiration but it has passed the maximum point.

Figure 4:
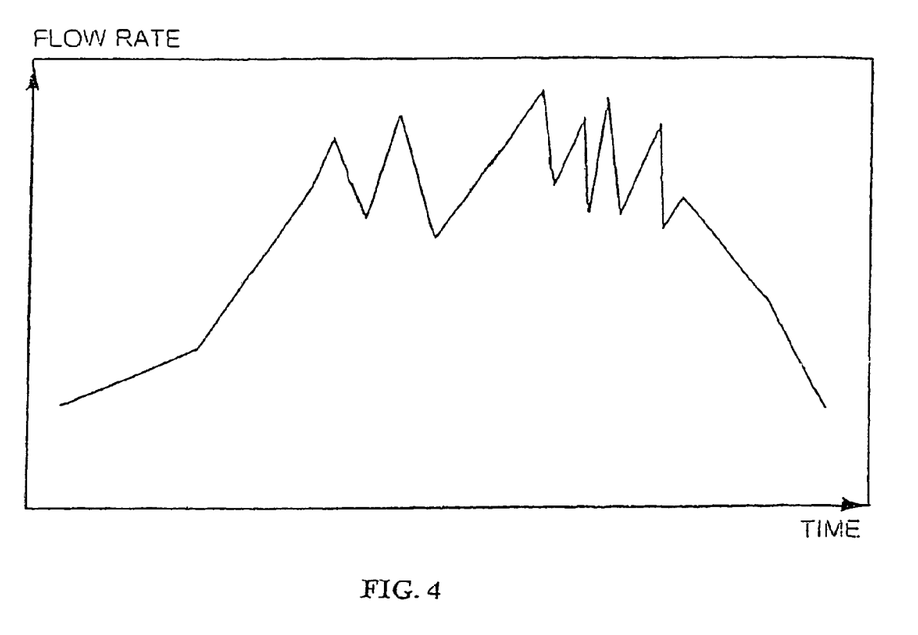
FIG. 4 is an example of a waveform for inspiration cycle with snoring.
Figure 5:
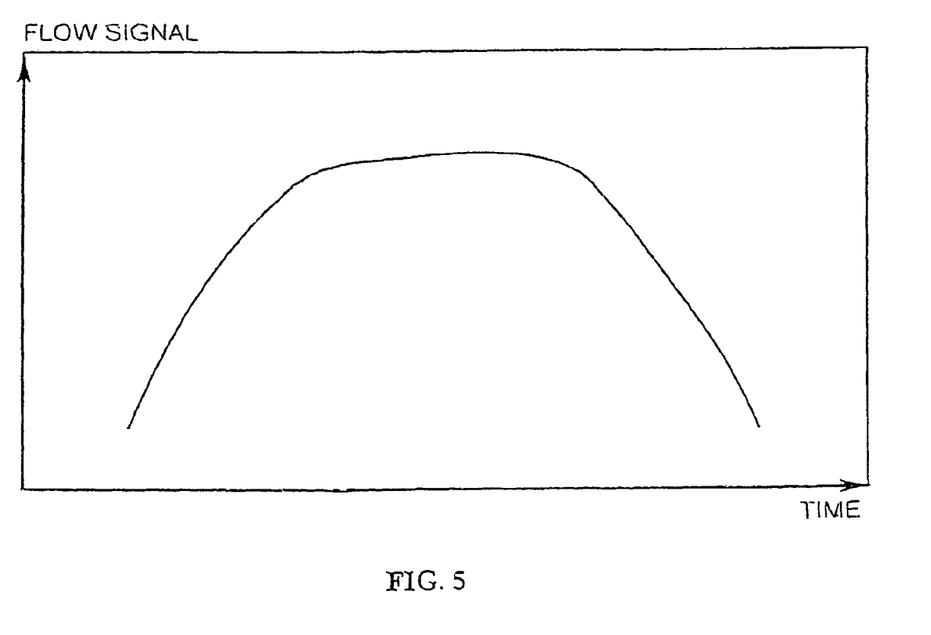
FIG. 5 is an example of a waveform for an inspiration with a UAR.

As mentioned previously, the present invention needs to detect three types of respiratory events, namely apneas and hypopneas, snoring, and inspiration flow limitation. The first type of events (apneas and hypopneas) is associated with reduction of inspiration flow and this can be resulted directly from the breath detection. Both snoring and inspiration flow limitation are more likely to occur during "abnormal" breath period. For a "normal" breath, the "shape" of signal on the top of inspiration flow appears "rounded" and relatively smooth. When snoring is present the high frequency flow signal is visible during inspiration as shown in FIG. 4. Inspiration flow limitation is defined as the event that the patient is unable to generate continuous flow increase during the first half of an inspiration period. As a result, the flow signal on the peak of inspiration flow becomes 'flat' as shown in FIG. 5. In flattening analysis, we determine a reference "flat" line which can be best fitted for the flow signal on the top of inspiration according the least square error (LSE), and the difference of the flow signal and the reference "flat" line during this period is then calculated as a flattening error. There are a number of flattening errors for different selections of the reference line. The flattening error with the smallest value is defined as a flattening index. The flattening index is then used to measure flow limitation, and the smaller the flattening index, the more severe is the inspiration flow limitation. A snoring index is also utilized to indicate the degree of the snoring. The snoring index is defined as measurement of the amount of high frequency signal on the top of inspiration flow.

C. Operation

Figure 6:
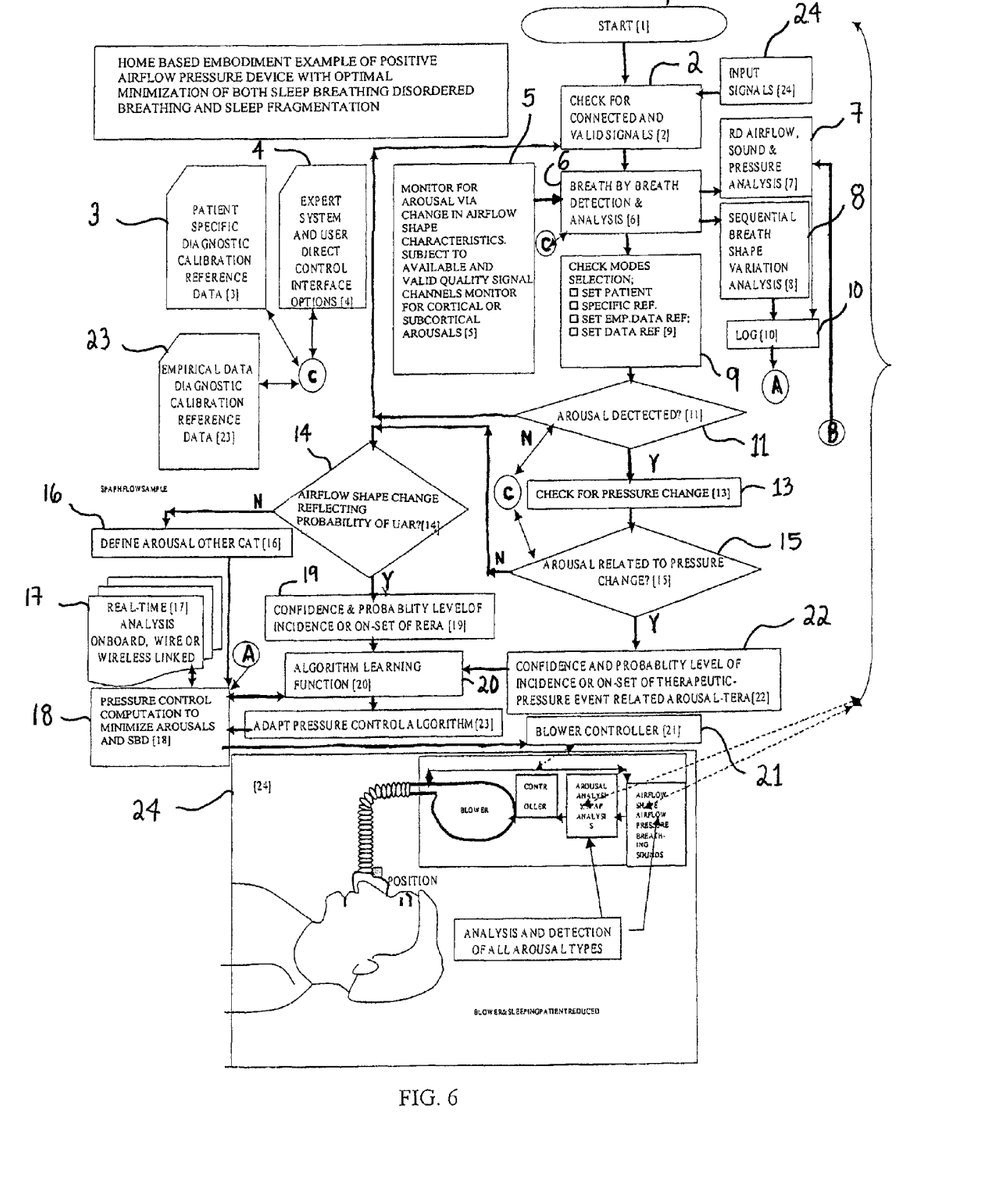
FIG. 6 is a flow diagram of one embodiment of the present invention.

An operational flow chart of one embodiment of the present invention is shown in FIG. 6. For the purposes of explanation only, the present invention will be described in an embodiment which is adapted for use with a CPAP machine. One skilled in the art can readily appreciate that the subject invention is easily adapted for use with, or incorporated within, other known therapeutic devices.

The present invention checks to make sure that it is receiving valid signals from its sensors. (box 2) Once the signal is verified, the signals are analyzed in order to determine if the onset of arousal has been detected. (boxes 5, 6, 7, and 8). The data used in the analysis is determined by the user.

In one embodiment, the present invention has the capability to use different forced oscillation treatment (FOT) to determine patient-specific threshold values for arousals and SBD. Results from the FOT are used to create templates which are used to determine the appropriate therapeutic response to avoid the onset of or eliminate the incidence of CSA, OSA, OSAHS, RERA, and TERA. (box 3) These templates or profiles are determined from patient-specific diagnostic studies or the appropriate FOT treatment at each particular stage in a subject's sleep or breathing status.

The present invention can obtain patient-specific FOT templates and profiles by utilizing forced oscillation of pressure, or changes in airflow pressure, to determine whether the changes in the airflow shape resulting from these subtle treatment changes are able to counteract the shape or profile characteristics indicative of the incidence or on-set of arousals (TERA or RERA) or OSAH and UAR. The present invention can vary the pressure change value and rate of change to countermeasure such events.

The present system provides a means to down-load from sleep laboratory studies or other types of previous sleep, respiratory and/or cardiac related investigations. The specific data is associated with a subject's breathing and sleep arousal parameters and is used to customize a gas delivery device to be more sensitive and accurate for both minimizing incidence of UARS, OSAHS, RERAs and TERAs, while still minimizing sleep fragmentation and optimizing sleep quality. (box 23) Each patient has a unique respiratory breathing circuit and associated pathways. Subsequently breathing waveforms during all stages of sleep of a patient will vary from patient to patient. The present invention ability to accommodate the patient's personal empirical data provides a means to produce more sensitive and effective treatment algorithm.

In one embodiment, if the onset of arousal has been determined (block 11), the present invention then determines if the CPAP has caused a pressure change (box 13) or if the event is caused by the existence of UAR (box 14). If there was no pressure change attributed to the CPAP machine, the present invention will likely determine that the onset of arousal was caused by RERA or another form of arousal. If there was a CPAP related pressure change, the present invention would make a determination if the onset of arousal was attributed to the pressure change or some other event (box 15). An appropriate remedy will then be selected based on the based on the physiological signals and the patient respiratory flow. (box 18)

In one embodiment, the present invention is able to utilize the determination to adapt the empirical data. (box 20) This enables the present invention to become more acutely sensitive to the physiological response of the patient.

The minimization of arousals includes the capability to automatically adjust the therapeutic treatment based on at least one index or derived data set wherein the index or derived data set can include the following:

Upper Airway Resistance (UAR), Respiratory Effort-Related Arousal (RERA), Therapeutic-control Event-Related Arousal (TERA), Respiratory Disturbance Index (RDI) Respiratory Arousal Index (RAI), Apnea-hypopnea index (AHI), Arousals (Micro-arousals), Arousals (Cortical), Arousals (subcortical), Arousals (Total), Total Arousal Time, Sleep stage, REM sleep, Sleep onset, Body movement, Percentage of arousal disrupted sleep (breakdown of all disrupted stages), Sleep efficiency Index, Sleep Fragmentation Index (new-SFI-Total Sleep Fragmenting arousals per hour), Airflow Shape trend, Airflow Shape Template Type, Flattening Index, Forced oscillation event, Pressure change event, Pressure change rate, Pressure change event curve, Pressure change event maximal and minima, Mixed Sleep Apnea events, Central Sleep Apnea events, Upper Airway Resistance Syndrome (UARS) events, Obstructive sleep apnea and hypopnea syndrome (OSAHS) events, Respiratory Effort-Related Arousals (RERA) with screen linked qualification of associated respiratory effort arousals, Therapeutic control Related Arousals (TERA) with screen linked qualification of pressure changes and arousals, Sleep Quality Index (new-hourly sleep index factor) Quality associated arousals, Oxygen Desaturation, Pulse Transit Time (PTT), Pulse Arterial Tone (PAT), Pulse Wave Amplitude (PWA), desaturation events and $SpO_2$ artifacts—accurate detection of cascaded desaturations, desaturations with $SpO_2$ artifacts inside, $SpO_2$ artifact start and end positions, detection sequences of respiratory events with partial or short recovery, classification of respiratory events with noisy or poor quality effort signals, detection episodes of Cheyne-Stokes breathing, Concordinance capability to allow score comparisons between any two designated data sets, Pneumotach calibrated flow, Thermal sensor flow, Sum of respiratory effort signals, EEG Arousals, PTT, Plethysmographic wave, Transthoracic impedance, Detection and allowance screen grid highlighting for an expanded set of automatic events to include the following events, Obstructive Sleep Apnea/Hypopnea event or syndrome (OSA, OSH, OSAHS), Respiratory effort related arousal, Central Sleep Apnea (CSA), Central Sleep Hypopnea (CSH), Cheyne-Stokes breathing, Hypoventilation, Yawn, Unstable breathing related to sleep state changes or onset of deeper stages of sleep, Swallowing, Coughing, Spontaneous or irregular but normal shaped breathing signals, Derived tidal volume (from nasal pressure or calibrated flow), Derived flow limitation index (from nasal pressure or calibrated flow), Derived snoring (from nasal pressure or calibrated flow), Derived diaphragmatic EMG amplitude, Derived upper airway resistance (from mask pressure, pharyngeal pressure and calibrated flow), Derived subcortical arousals (from PTT or pleth wave amplitude), Breathing mask and/or airflow sound analysis with segmentation into various breathing disorders such as cough, wheeze, strider, apnea and hypopnea.

For every selected event (combination of a set of expanded group of events from above and current set of events), a user is allowed to select the set of measurement signals and to set the parameters of detection for the event. This enables the present invention to use more than one signal at the same time to detect an event and more than one scenario to detect an event. The following are examples of defined events:

RERA—
 1. Break in the flat inspiratory profile after a few flow limited breaths
 2. Frequency shift in EEG, amplitude increase in EMG
 3. Subsequent leg movement activity
 4. No pressure augmentation (CTRL signal)

Leg Movement Related Arousal—
 1. Increase in leg movement activity
 2. Frequency shift in EEG, amplitude increase in EMG
 3. Break in the inspiratory profile not necessarily during inspiration
 4. No pressure augmentation (CTRL signal)

Spontaneous Arousal—
 1. Frequency shift in EEG, amplitude increase in EMG
 2. No increase (or after EEG/EMG changes) in leg movement activity
 3. Break in the inspiratory profile not necessarily during inspiration
 4. No pressure augmentation (CTRL signal)

Pressure Augmentation Related Arousal—
 1. Pressure increase according to the titration algorithm
 2. Subsequent frequency shift in EEG, amplitude increase in EMG
 3. No increase (or after EEG/EMG changes) in leg movement activity
 4. Break in the inspiratory profile not necessarily during inspiration The present invention significantly reduces arousal by restricting the application of pressure treatment until a patient is in a stage of sleep where this pressure is not experienced or causes no adverse patient discomfort. Pressure of air delivered to a patient is ramped up or down depending upon the patient's sleep state. Pressure is ramped up slowly while physiological parameters are monitored. Once the physiological parameters indicate the onset of arousal (microarousal) the pressure is maintained or reduced until the patient is in deeper levels of sleep enabling continued ramping up of pressure. Pressure is also ramped downwards accordingly.

The controller 12 is implemented as a combination of rules for pressure change. Every pressure change rule specifies the magnitude and sign of a pressure change and the allowed range of pressure values within which the pressure change can be activated as well a number of additional parameters including time constants, timeouts and forced oscillation logic. Every pressure change rule is activated if a respective logical combination of its conditions is true. In one embodiment, pressure change rules are combined via logical OR—pressure changes if any single rule in the set of rules is satisfied. If more than one rule is satisfied the rule with a higher priority takes precedence.

Conditions for various pressure change rules represent a number of physiological scenarios:
 Flow limitation (flattening) over a number of subsequent breaths—pressure increase
 Flow limitation (flattening) and snoring over a number of subsequent breaths—pressure increase
 Snoring over one or two breaths—pressure increase
 Hypopneas—pressure increase (it is recommended to use additional information such as PTT, band or mattress signals to discriminate obstructive vs central hypopneas)
 Detection of apnea start—start forced oscillation
 Low level of upper airway conductance with forced oscillation—pressure increase (obstructive apnea detected)
 No flow limitation (rounded breath shape)—gradual pressure reduction
 Large leak—pressure reduction to 4 cmH2O
 No airflow over 3 minutes—pressure reduction to 4 cmH2O The present invention is capable of overcoming varying arousal dependent factors by applying adaptive algorithm techniques. The adaptive algorithm technique has the capability to apply empirical clinical data to establish standard threshold configurations, which in turn determine a device's response and performance in terms of gas delivery characteristics. The adaptive algorithm technique also has the capability to apply a set of threshold characteristics.

In one embodiment, these threshold characteristics can vary parameters such as the rate of pressure change, the absolute amount of pressure change, the minimum delivered pressure values, the maximum delivered pressure values. These rates and absolute pressure changes can vary in accordance to various states of said patient including (for example only) the patient's current sleep state or the patient's relative blood pressure or arrhythmia detection. The present invention can be configured in a predetermined mode of operation where the algorithm adaptation function can be disabled and replaced by an algorithm that relies on a fixed set of reference data designed to predict the onset or detect the occurrence of TERA and RERA, while minimizing sleep breathing disorders.

In one embodiment, the present invention enables medical specialists to set various thresholds, which may prevent undesirable medical conditions for each particular patient. For example, if central sleep apnea is detected in combination with an increase or undesirable change or measure in ECG, pulse-wave or arrhythmia, the operation of the gas delivery device is augmented to stabilize the patient's condition. In some instances this stabilization may include the immediate cessation of pressure delivery. During events such as central sleep apnea (cessation of breathing activated by the brain commands versus airway obstruction), for example, forced pressure delivery without airway obstruction may otherwise aggravate the subject's blood pressure or cardiac function.

The present invention is capable of operating with or without any previous patient data (a specific airflow shape characteristics or various thresholds, for example). In the case where a subject has no previous data or threshold indications the present invention could commence operation with standard empirical data threshold settings. During device generated pressure changes or whenever there is a respiratory disturbance the present invention can adapt its control characteristics to minimize the respiratory and arousal disturbance.

In one embodiment, monitoring of arousals enables the subject invention to augment a CPAP's sleep disorder detection capabilities. False negatives often occur during mild hypopnea events. There is typically such minimal airflow limitation that CPAP machines are unable to detect the breathing disorder. However, such mild events often create sufficient UAR to cause arousal in a patient. The detection of the onset of such arousals enables the present invention to initiate a corrective response from the CPAP unit, even though the CPAP is unable to detect the event.

In one embodiment, a treatment mode includes utilizing breathing pattern templates stored in the table to augment current CPAP settings. These dynamically allocated breathing pattern templates supplement the CPAP algorithm by changing the control characteristics of the CPAP unit. The templates satisfy the particular patient's pressure requirements while optimizing the patient's sleep and minimizing patient arousal.

In one embodiment, the present invention enables the commencement of treatment to be determined by a pre-defined state of sleep, arousal activity level, and/or pre-determined sleep disordered breathing activity. One of the difficulties experienced by patients with existent state of the art gas delivery treatment devices is the discomfort experienced from the positive air pressure applied to a patient, while they are attempting to fall asleep.

Existent state of the art devices have the capability to provide a delayed start function. This delay function provides a time delay before the treatment pressure slowly increases or ramps up to a prescribed value of start pressure. However, patients are not always able to predict their sleep onset time as drowsiness of a patient varies from one night to the next. The concept of a prescribed delay time can also provide a psychological anxiety, as the patient is always aware that if they do not succumb to a satisfactory sleep state in an appropriate amount of time, they risk experiencing the unpleasant sensation of excessive positive air pressure during their sleep preparation time.

The present invention enables the detection of sleep state and/or arousals as a mean to determine pressure activation. Treatments are applied only when the patient is in a preselected or deep state of sleep and subsequently is oblivious to the said commencement of treatment. The determination of sleep state can be the methods which are known in the art, including those methods disclosed in the U.S. Pat. No. 6,397,845, the contents of which are hereby incorporated in its entirety.

In one embodiment, a present invention has an integrated diagnostic and treatment mode where adjustments to the delivered air are changed in real time (i.e. changes are instantaneously made depending upon the values of the monitored parameters).

The present invention's control algorithm has the capability to be adapted during real-time operation based on any combination of a) empirical clinical data, b) individual patient collected or collected data (from diagnostic study within sleep laboratory or other alternative site or c) real-time monitored and analyzed data.

D. Alternative Embodiments

Figure 7:
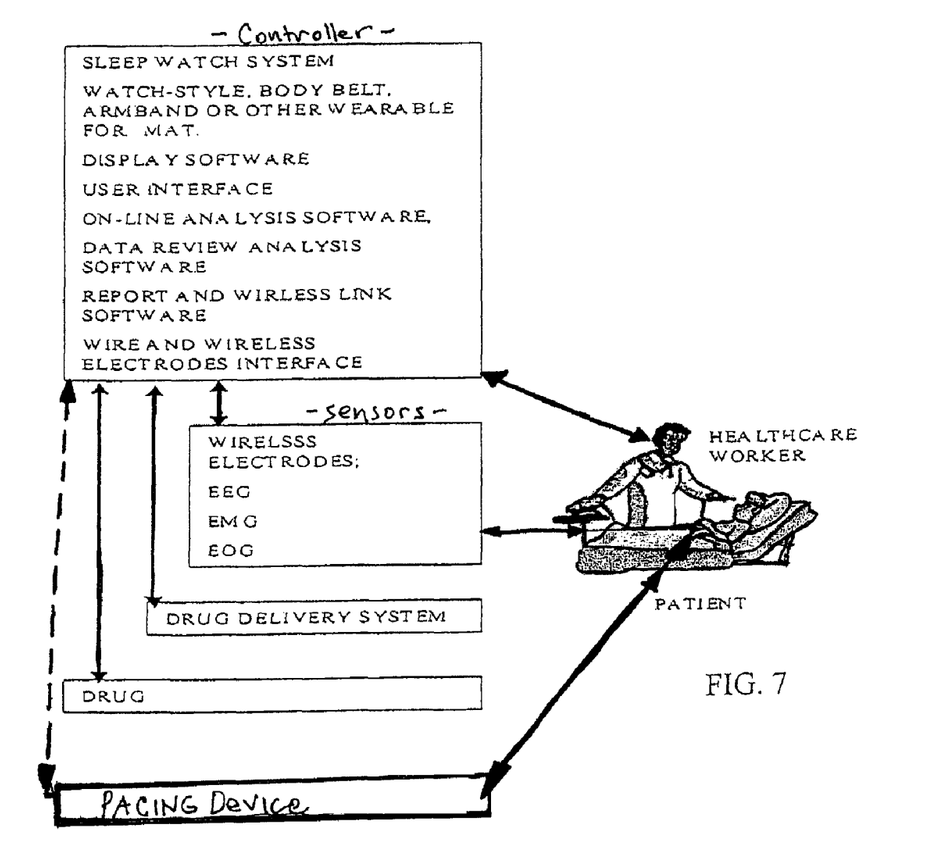
FIG. 7 is a schematic diagram of one embodiment of the present invention.

In one alternative embodiment, as shown in FIG. 7, the present invention is used to deliver medication to a patient. Previous methods for determining sedative or tranquilizer dosage requirements for a subject are often estimated on a generalized patient group or a specific sample patient group.

A subject's sleep or vigilance propensity is highly complex and dependent on many parameters. It has been shown, for example that a person's sleep propensity can be related to sleep deprivation, alcohol, anxiety, stress, environmental factors, body mass index, gender, hereditary and other factors.

The consequence of over-sedation include increased recovery time, attention deficit risks associated with excessive drowsiness, increased costs of drugs, and reduction in the quality of life due to the extended drowsy state of a subject.

The drug administration can deliver a range of drugs utilizing methods such as (but not limited to) orally, transdermal, fluid drip delivery, vapor delivery and gas delivery. Utilizing the integration of a drug delivery system with the present invention, a drug dosage can be optimized for a predetermined level or an appropriate level of drowsiness, vigilance or attention state.

The user or health-care provider could adjust drug administration dosage in consultation with the patient and the monitored patient data.

A further capability of the present invention is to contain sensors such as sensitive movement devices that together with signal analysis (such as but not limited to spectral, phase and amplitude) can detect shaking, tremors and other signs indicating appropriate drug usage. In the case of Parkinson's and other disease types the present system could be programmed to administer, for example, adequate drugs to minimize tremors and shaking, while at the same time provide the subject with a degree of vigilance during the day and sleep quality during the night that is most conducive to each individual's quality of life requirements or desires.

The present invention can be adapted in a number of configurations with different combination of physiological recording channels, sensors, analysis, storage and display capabilities. These capabilities could vary subject to the specific disease or disorder being treated, along with each subject's specific health-specialist requirements for information.

In another alternative embodiment, as shown in FIG. 7, the present invention includes a pacemaker control algorithm which minimizes RERA and TERA while optimizing a subject's heart pacing. The present invention enables the detection of RERA and TERA from the electrocardiogram or pulse-wave signals, for example. Alternatively, more comprehensive signals can be deployed. The present invention enables the conventional optimization of ECG pacing while at the same time minimizing arousals and sleep fragmentation. Pacemaker control can also be utilized to assist in the elimination of some sleep disordered breathing. The present invention can provide important feedback as to the causation of sleep fragmentation such as inappropriate pacemaker control causing promotion of sleep fragmenting arousals.

The present invention is also able to monitor heart rate, blood-pressure variations and sleep fragmentation arousals throughout sleep and determine whether these said variations relate to normal sleep physiology, or whether these changes suggest modification of pacemaker control in order to optimize heart function, while at the same time minimizing sleep fragmentation.

In another embodiment, the present invention has the capability to provide optimal sleep during oxygen concentration treatment by utilizing cortical, subcortical, airflow shape or waveform characteristics as a marker for optimizing the treatment. The present invention can control the titration algorithm to minimize RERA and TERA while optimizing a subject's breathing therapy. The present invention enables the detection of RERA and TERA by monitoring any combination of breathing mask or hose sounds, airflow or pressure signals. Alternatively more comprehensive signals can be deployed. SOC enables the conventional optimization of blood-gas status of a subject, while minimizing arousals. An inappropriate mixture of oxygen and air, or rate of delivery of gas to a subject could promote arousals, for example.

Inappropriate gas delivery could in turn cause mechanical or chemical receptors within the patient's breathing anatomy to activate sleep fragmentation arousals (TERA). The monitoring of the airflow wave shape can be used to predict the onset or incidence of TERA or RERA and allow the gas treatment to be controlled in such a manner to minimize such arousals (while still optimizing breathing therapy).

In one embodiment, the present invention is utilized as purely a diagnostic tool for determining sleep disordered breathing and sleep quality. The present invention is adapted to record, meter, index or display, in real time or on a replay or review basis, a number of sleep or arousal related physiological data or statistics. Statistics and indexes such as RAI, AHI, RERA, RDI, arousals, sleep fragmentation, or sleep architecture index are derived from the monitored parameters and this information is stored for analysis.

In one embodiment, monitored physiological parameters monitored which were utilized to determine the statistics and indexes may also be stored in order to assist in the analysis. The present invention can also include graphical and statistical tools which are known in the art to enable a user to manipulate and display raw data or derived values in a meaningful format. In one embodiment, the present invention has the capability of displaying raw data and then using visual clues to mark the occurrence of an event such as arousal in the raw data. The present invention can also link an event or events to specific index values or derived values which reflect the occurrence of the event.

The matter set forth in the foregoing description and accompanying drawings is offered by way of illustration only and not as a limitation. While a particular embodiment has been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A method of providing a therapeutic treatment to a patient, the method comprising:
    setting a treatment level;
    monitoring a physiological parameter that is an indicator of arousal;
    determining if the monitored physiological parameter indicates that an arousal is about to take place; and
    adjusting the treatment level to avoid arousal.

2. The method of claim 1, and further comprising the step of determining if an arousal is caused by upper airway resistance (UAR) or by the treatment level.

3. The method of claim 1, wherein the step of adjusting includes varying treatment levels until a treatment level is determined which does not cause arousal.

4. The method of claim 3, and further comprising the step of storing the treatment level which does not cause arousal.

5. The method of claim 1, wherein the step of monitoring includes monitoring of cortical or sub-cortical activity.

6. The method of claim 5, wherein the step of determining includes detecting a shift to alpha or theta EEG activity from a slower background frequency.

7. The method of claim 1, wherein the step of determining includes detecting a drop in the pulse transit time (PTT).

8. The method of claim 1, and further comprising computing an index value from a plurality of monitored parameters and utilizing the index value to predict onset of arousal.

9. The method of claim 1, wherein the step of determining includes comparing a patient airflow waveform with a plurality of templates which depict onset of arousal.

10. The method of claim 1, and further comprising the additional step of providing a table correlating a combination of physiological events to an optimum adjustment of the treatment level which minimizes arousal.

11. The method of claim 10, wherein the step of determining includes detecting whether an event is associated with central apnea or obstructive apnea.

12. The method of claim 1, wherein the step of determining includes utilizing patient specific data to determine thresholds for arousal.

13. The method of claim 1, wherein the step of determining includes comparing cortical and subcortical activity to determine periodic leg movement-related arousals.

14. The method of claim 1, and further comprising the additional step of determining a patient's sleep state and regulating treatment based on a patient's sleep state.

15. The method of claim 1, and wherein the step of determining includes detecting a change in measure of residual carbon dioxide levels, residual nitric oxide levels, or residual oxygen levels.

16. The method of claim 1, and further comprising the additional step of transferring data to a treatment device to enable the treatment device to determine a treatment parameter which minimizes arousals or sleep breathing disorders.

17. A method of controlling delivery of a gas to a patient comprising:
monitoring a physiological parameter;
delivering gas at a set level;
determining from the physiological parameter if an arousal is about to take place;
determining if the arousal that is about to take place is caused by upper airway resistance or gas delivery;
adjusting the level of delivered gas based on whether the arousal is attributed to upper airway resistance or gas delivery.

18. The method of claim 17, and further comprising using a forced oscillation treatment to determine threshold levels for arousal.

19. The method of claim 17, and further comprising the additional step of determining the onset of Respiratory Effort Related arousal.

20. The method of claim 17, and further comprising the step of determining the onset of obstructive sleep apnea-hypopnea.

21. The method of claim 17, and further comprising providing a table having a plurality of entries which define an onset of an event based on a set of values for a plurality of different monitored physiological parameters.

22. The method of claim 17, and further comprising the additional step of adjusting the pressure level-of the delivered gas based on an index value derived from at least one of the plurality of monitored physiological parameters.

23. The method of claim 17, and further comprising the step of determining sleep quality.

24. The method of claim 17, and further comprising the step of determining cheynes-stokes respiration.

25. The method of claim 17, and further comprising providing a table linking a plurality of values from the monitored parameters to an event, and updating the table to accommodate a patient's sensitivity.

26. The method of claim 17, wherein the step of determining includes high bandwidth monitoring of airflow waveforms or pressure waveforms to determine arousal or sleep breathing disorders.

27. The method of claim 17, wherein the step of determining includes analyzing pulse transit time, blood pressure, and ECG signals to determine the onset of arousal.

28. The method of claim 17, wherein the step of determining includes analyzing a patient's breath to determine a periodic breathing event.

29. The method of claim 17, and further comprising the step of determining the existence of oral breathing and wherein the step of adjusting includes compensating for oral breathing.

30. An apparatus comprising:
a sensor for detecting a physiological signal;
a therapeutic device having an adjustable treatment level; and
a controller in communication with the sensor and the therapeutic device, the controller adapted to detect, from the detected physiological signal, if an arousal is about to take place, and to adjust treatment level to avoid arousal.

31. The apparatus of claim 30, wherein the therapeutic device is a gas delivery device.

32. The apparatus of claim 30, wherein the therapeutic device is an infusion device.

33. The apparatus of claim 30, wherein the therapeutic device is a cardiac pacemaker system.

34. The apparatus of claim 30, and further comprising a memory device containing a table correlating the values of a plurality of physiological parameters to onset of arousal.

35. The apparatus of claim 30, and further comprising a memory device containing a table correlating onset of arousal with an appropriate treatment level.

36. The apparatus of claim 30, wherein the controller is also adapted to predict the onset of obstruction sleep apnea-hypopnea.

37. The apparatus of claim 30, wherein the controller is also adapted to perform a test varying treatment level to determine sensitivity of patient to treatment related arousal.

38. The apparatus of claim 30, wherein the controller is also adapted to monitor sleep quality.

39. The apparatus of claim 30, wherein the controller is also adapted to create an index value from a plurality of different physiological signals and to adjust the treatment level based on the index value.

40. A gas delivery device comprising:
a plurality of sensors for monitoring a plurality of physiological parameters; a gas delivery device having an adjustable pressure level; and
a controller in communication with the sensor and the gas delivery device, the controller adapted to determine if an arousal is about to take place resulting from RERA or from TERA, and to adjust the pressure level of the gas delivery device accordingly.

41. The gas delivery device of claim 40, wherein the gas delivery device is a CPAP machine.

42. The gas delivery device of claim 40, wherein the gas delivery device is a ventilator.

43. The gas delivery device of claim 40, wherein the gas delivery device is an oxygen concentrator.

44. The gas delivery device of claim 40, wherein the controller is also adapted to obtain and store patient-specific physiological parameters which indicate the onset of arousal.

45. The gas delivery device of claim 40, wherein the plurality of sensors communicate with the controller utilizing a wireless technology.

* * * * *